(12) United States Patent
Namiki et al.

(10) Patent No.: US 7,771,066 B2
(45) Date of Patent: Aug. 10, 2010

(54) LIGHT PULSE MULTIPROCESSING UNIT, LIGHT PULSE GENERATOR USING THE SAME, AND LIGHT PULSE MULTIPROCESSING METHOD

(75) Inventors: Mitsuru Namiki, Hanno (JP); Yuji Sakai, Tokyo (JP)

(73) Assignee: Olympus Corporation, Tokyo (JP)

( * ) Notice: Subject to any disclaimer, the term of this patent is extended or adjusted under 35 U.S.C. 154(b) by 431 days.

(21) Appl. No.: 11/723,848

(22) Filed: Mar. 22, 2007

(65) Prior Publication Data
US 2007/0171423 A1 Jul. 26, 2007

(30) Foreign Application Priority Data
Mar. 28, 2005 (JP) ............................. 2005-092036
Mar. 24, 2006 (JP) ............................. 2006-082978

(51) Int. Cl.
G02B 5/08 (2006.01)
G02B 7/192 (2006.01)
G02B 7/182 (2006.01)

(52) U.S. Cl. ...................................... 359/848; 359/850

(58) Field of Classification Search ................. 359/848, 359/833, 837, 850
See application file for complete search history.

(56) References Cited

U.S. PATENT DOCUMENTS
2003/0012236 A1* 1/2003 Hasson ........................ 372/25

* cited by examiner

*Primary Examiner*—Scott J Sugarman
*Assistant Examiner*—Brandi N Thomas
(74) *Attorney, Agent, or Firm*—Pillsbury Winthrop Shaw Pittman, LLP

(57) ABSTRACT

A light pulse multiprocessing unit has a half mirror and N delay elements, each having a refractive index n. The N delay elements are arranged on one side of the half mirror from one end of the half mirror toward the other end and have thicknesses $\Delta, 2\Delta, \ldots, 2^{N-1}\Delta$ different from each other, where $\Delta$ is the smallest thickness. The half mirror is placed in parallel in the proximity of an intermediate position between two mirrors and the N delay elements are arranged between one of the mirrors and the half mirror. Each of the N delay elements is a plane-parallel plate and is placed at an angle such that the direction of the normal line of the surface of the plane-parallel plate is different from a direction followed from one end of the half mirror toward the other end.

7 Claims, 12 Drawing Sheets

$2^N$ LIGHT PULSES

BETWEEN B1-O2

BETWEEN A1-O2

BETWEEN B2-O3

BETWEEN A2-O3

O3 JUST AFTER PASSAGE

8 LIGHT PULSES

LIGHT PULSE MULTIPROCESSING UNIT, LIGHT PULSE GENERATOR USING THE SAME, AND LIGHT PULSE MULTIPROCESSING METHOD

This application is based on Japanese Application No. 2005-092036 filed in Japan on Mar. 28, 2005, and No. 2006-082978 filed in Japan on Mar. 24, 2006, and claims benefits of the latter. The contents of these Japanese applications are incorporated herein by reference.

BACKGROUND OF THE INVENTION

1. Field of the Invention

This invention relates to a light pulse multiprocessing unit producing a light pulse train, a light pulse generator using this unit, and a light pulse multiprocessing method.

2. Description of Related Art

A conventional light pulse generator is set forth, for example, in US 2003/0012236A1. The structure and function of the light pulse generator will be briefly explained with reference to FIGS. 1 and 2. The light pulse generator shown in FIG. 1 is constructed with a pulse light source 51, a delay structure 52, a condenser lens 53, and a wave-guide 54. The delay structure 52, as shown in FIG. 2, has a step-like contour. This can be thought of as an arrangement of a plurality of plane-parallel plates that are equal in refractive index but different in thickness. The plane-parallel plates are arranged at equal intervals in a direction perpendicular to the optical axis. The difference between thicknesses of adjacent plane-parallel plates, measured along the optical axis, is kept constant. When a light pulse emitted from the pulse light source 51 is rendered incident as a plane wave on the delay structure 52, a change is caused to an optical path length in accordance with the thickness of the plane-parallel plate through which the light pulse passes. Specifically, as indicated by numerals $55_1, 55_2, \ldots, 55_n$, a wavefront is stepwise modulated. Such light is collected by the condenser lens 53, and thereby a light pulse train is transmitted to the wave-guide 54.

SUMMARY OF THE INVENTION

The light pulse multiprocessing unit according to the present invention has a splitting means for splitting incident light to produce transmitted light and reflected light, a pair of light deflecting means arranged on one side and the other side of the splitting means so that the transmitted light and the reflected light, split by the splitting means are deflected and are combined again at a common place on the splitting means, and delay means provided on at least one of the one side and the other side of the splitting means, for making a substantial optical path difference between optical paths of light split by the splitting means and combined again at the common place on the splitting means to impart a time delay to light traveling along the one side of the splitting means. Here, the substantial optical path difference is that, for example, the difference is made between actual optical path lengths by elements, each having a refracting index n and a different thickness in a portion through which light is transmitted, or by elements provided by a combination of a plurality of reflecting mirrors and that the refractive index is properly changed to substantially make the difference between optical path lengths, and includes a combination of these.

In the light pulse multiprocessing unit of the present invention, it is desirable that N delay means are arranged on the one side of the splitting means and when the substantial optical path difference due to a first delay means is denoted by D, the substantial optical path difference due to an Nth delay means is $2^{N-1}D$.

In the light pulse multiprocessing unit of the present invention, it is desirable that individual delay means are delay elements, each having a refractive index n, and portions of the delay elements through which light is transmitted from the first delay means to the Nth delay means are different in thickness from one another.

In the light pulse multiprocessing unit of the present invention, it is desirable that each of the delay means is provided with a plurality of mirrors and spacings between the plurality of mirrors are different in the range from the first delay means to the Nth delay means.

In the light pulse multiprocessing unit of the present invention, it is desirable that the pair of light deflecting means are a first mirror and a second mirror, arranged parallel to each other.

In the light pulse multiprocessing unit of the present invention, it is desirable that the light deflecting means and the delay means include wedge prisms.

In the light pulse multiprocessing unit of the present invention, it is desirable that the pair of light deflecting means include a pair of wedge prisms.

The light pulse multiprocessing unit according to the present invention has a half mirror and N delay elements, each having a refractive index n. The N delay elements are arranged on one side of the half mirror from one end of the half mirror toward the other end and have thicknesses different from each other. When the smallest thickness is represented by $\Delta$, individual thicknesses of the N delay elements are $\Delta, 2\Delta, \ldots, 2^{N-1}\Delta$.

In the light pulse multiprocessing unit of the present invention, it is desirable that a first mirror and a second mirror that are arranged parallel and opposite to each other are provided; the half mirror is placed parallel to the first mirror and the second mirror in the proximity of an intermediate position between the first mirror and the second mirror; the N delay elements are arranged between the first mirror and the half mirror; and each of the N delay elements is a plane-parallel plate and is placed at an angle such that the direction of the normal line of the surface of the plane-parallel plate is different from a direction followed from the one end of the half mirror toward the other end.

In the light pulse multiprocessing unit of the present invention, it is desirable that a first mirror and a second mirror that are arranged parallel and opposite to each other are provided; the half mirror is placed parallel to the first mirror and the second mirror in the proximity of an intermediate position between the first mirror and the second mirror; the N delay elements are arranged between the first mirror and the half mirror; each of the N delay elements is a prism unit including two wedge prisms of identical shape; the two wedge prisms in the prism unit are arranged to overlap so that one of surfaces making the smallest apex angle of one prism comes in contact with a corresponding surface of the other prism; and prism units are such that areas of surfaces in contact are different from one another.

In the light pulse multiprocessing unit of the present invention, it is desirable that a mirror placed parallel to the half mirror is provided; the N delay elements are arranged on the opposite side of the mirror with respect to the half mirror and are constructed with wedge prisms of identical shape, one for each element; and the wedge prisms are arranged so that surfaces subtending the apex angles are located on the half mirror side and distances from the surfaces subtending the apex angles to the half mirror are different from one another.

In the light pulse multiprocessing unit of the present invention, it is desirable that separate N delay elements are provided and arranged at equal intervals from one end of the half mirror toward the other end on the opposite side of the N delay elements with respect to the half mirror; the N delay elements and the separate N delay elements are constructed with wedge prisms of identical shape, one for each element; the wedge prisms of the N delay elements are arranged so that surfaces subtending apexes with the smallest apex angles are located on the half mirror side and distances from the surfaces subtending the apexes to the half mirror are different from one another; and the wedge prisms of the separate N delay elements are arranged so that surfaces subtending apexes with the smallest apex angles are located on the half mirror side and distances from the surfaces subtending the apexes to the half mirror are identical.

In the light pulse multiprocessing unit according to the present invention, it is desirable that the wedge prisms of the prism unit can be moved parallel along the surfaces coming in contact with each other.

In the light pulse multiprocessing unit according to the present invention, it is desirable that the half mirror includes a plane-parallel plate with predetermined thickness and a semi-transmissive reflecting film provided on one surface of the plane-parallel plate; of the first mirror and the second mirror, the mirror located on the side that the semi-transmissive reflecting film of the half mirror is provided includes a plane-parallel plate equal in thickness to the plane-parallel plate constituting the half mirror and a reflecting film provided on the surface, lying on the opposite side of the half-mirror-side surface, of the plane-parallel plate; and of the first mirror and the second mirror, the mirror located on the opposite side of the side that the semi-transmissive reflecting film of the half mirror is provided includes a plane-parallel plate and a reflecting film provided on the half-mirror-side surface of the plane-parallel plate.

In the light pulse multiprocessing unit according to the present invention, it is desirable that the half mirror includes a plane-parallel plate with predetermined thickness and a semi-transmissive reflecting film provided on the mirror-side surface of the plane-parallel plate; and the mirror includes a plane-parallel plate equal in thickness to the plane-parallel plate constituting the half mirror and a reflecting film provided on the surface, lying on the opposite side of the half-mirror-side surface, of the plane-parallel plate.

In the light pulse generator according to the present invention, it is desirable to have the light pulse multiprocessing unit of the present invention and a pulse light source.

The light pulse multiprocessing method according to the present invention is to split incident light to produce transmitted light and reflected light; change an optical path length in each of a first optical path along which the transmitted light travels and a second optical path along which the reflected light travels; and combine light passing through the first optical path with light passing through the second optical path to impart a time delay to combined light. The amount of change of the optical path length in the first optical path is different from that of the optical path length in the second optical path.

In the light pulse multiprocessing method of the present invention, it is desirable that the reflection and splitting-combination of the transmitted light are alternately performed in the first optical path, while the reflection and splitting-combination of the reflected light are alternately performed in the second optical path.

In the light pulse multiprocessing method of the present invention, it is desirable that the splitting-combination, refraction, and reflection of the transmitted light are performed in preset order in the first optical path, while the splitting-combination, refraction, and reflection of the reflected light are performed in preset order in the second optical path.

In the light pulse multiprocessing method of the present invention, it is desirable that the refraction and splitting-combination of the transmitted light are alternately performed in the first optical path, while the refraction and splitting-combination of the reflected light are alternately performed in the second optical path.

According to the light pulse multiprocessing unit, the light pulse generator using this unit, and the light pulse multiprocessing method of the present invention, the light pulse train of high combination efficiency can be obtained. Moreover, the pulse intervals of the light pulse train can be arbitrarily set.

These and other features and advantages of the present invention will become apparent from the following detailed description of the preferred embodiments when taken in conjunction with the accompanying drawings.

DETAILED DESCRIPTION OF THE PREFERRED EMBODIMENTS

Description of the First Aspect

FIGS. 3A, 3B, 3C, 3D, 3E, and 3F are views of a schematic structure of the light pulse multiprocessing unit of the first aspect in the present invention, showing the general view and the delay states of a light pulse P on a route B1-O2, a light pulse $P_1$ on a route A1-O2, light pulses P and $P_1$ on a route B2-O3, light pulses $P_2$ and $P_3$ on a route A2-O3, and light pulses P, $P_1$, $P_2$, and $P_3$ immediately after light is split and combined at a preset place O3, respectively.

The light pulse multiprocessing unit of the first aspect includes a first mirror 11, a second mirror 12, a half mirror 2, and N delay elements 311, 312, ..., 31N, each having a refractive index n. The first mirror 11 and the second mirror 12 are arranged parallel and opposite to each other. The half mirror 2 is placed parallel to the first mirror 11 and the second mirror 12 in the proximity of an intermediate position between the first mirror 11 and the second mirror 12.

The half mirror 2 splits (amplitude-splits) the light pulse into a reflection-side pulse and a transmission-side pulse when the light pulse is rendered obliquely incident on the half mirror 2. One of the light pulses that have been split is reflected at the first mirror 11. The other light pulse is reflected at the second mirror 12. Light reflected by the first mirror 11 and the second mirror 12 is combined at a common place on the half mirror 2. The light pulse that has been combined is split again by the half mirror 2. In this way, in the light pulse multiprocessing unit of the first aspect, the operation ranging from the splitting of the light pulse by the half mirror 2 to the combination of the light pulses on the half mirror 2 is repeated N times. The first mirror 11, the second mirror 12, and the half mirror 2 have predetermined sizes so that the splitting and combination can be performed a plurality of times. The light pulse multiprocessing unit constructed as mentioned above is arranged and used so that the first mirror 11, the second mirror 12, and half mirror 2 are inclined with respect to the incident optical path of the light pulse.

Figure 1:
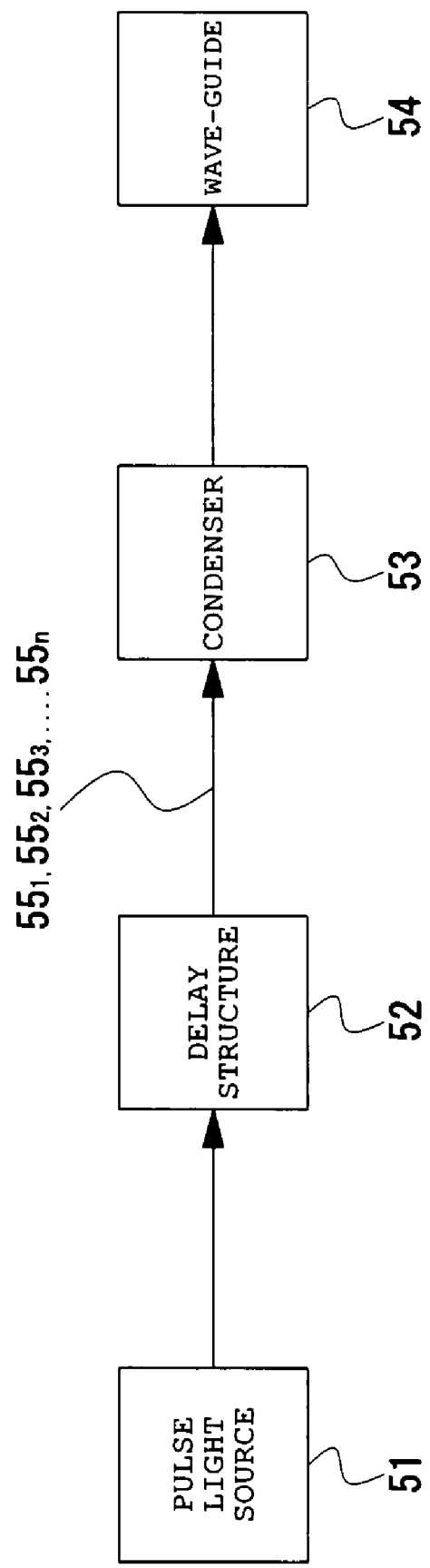
FIG. 1 is a block diagram showing a schematic structure of an example of a conventional light pulse generator.
Figure 2:
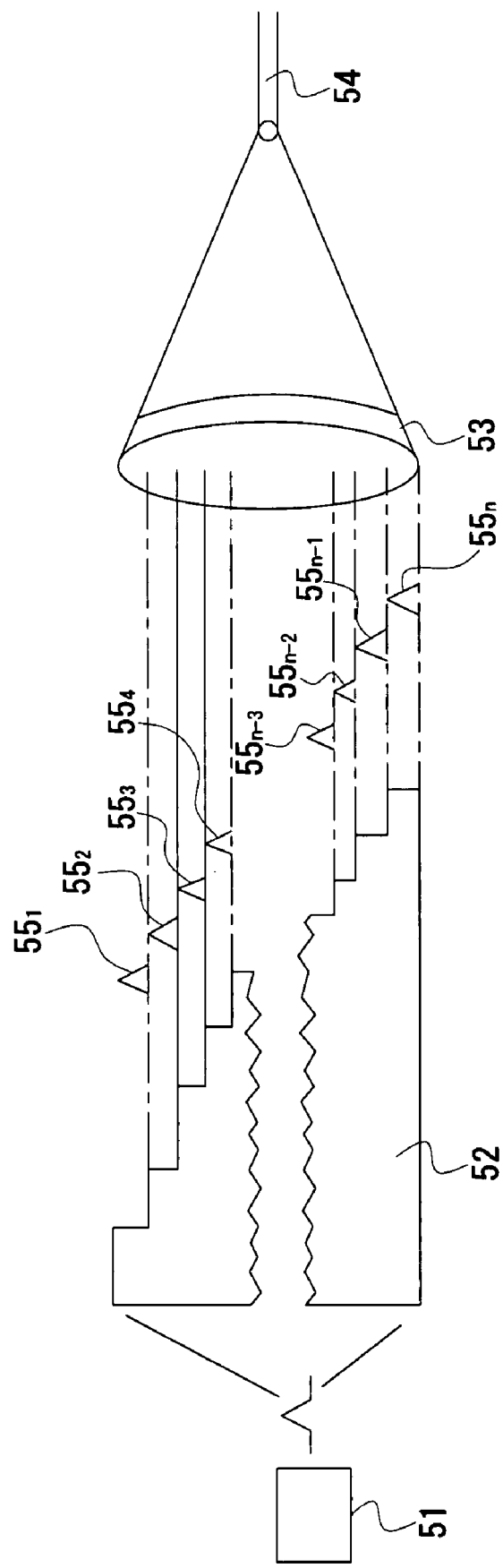
FIG. 2 is an explanatory view showing a delay structure producing a light pulse train in the light pulse generator of FIG. 1.
Figure 3A:
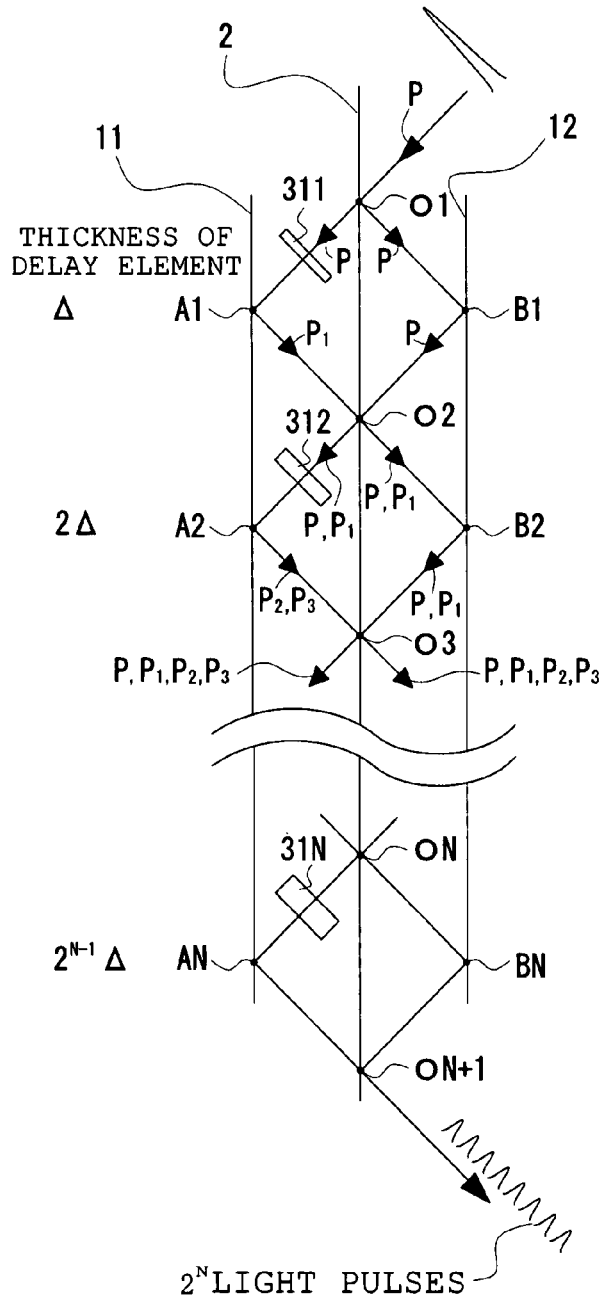
FIGS. 3A, 3B, 3C, 3D, 3E, and 3F are views of a schematic structure of the light pulse multiprocessing unit of a first aspect in the present invention.
Figure 3B:

The N delay elements 311, 312, ..., 31N are constructed with plane-parallel plates. Individual plane-parallel plates use glass materials of the same refractive index n. The plane-parallel plates have thicknesses of $\Delta$, $2\Delta$, ..., $2^{N-1}\Delta$. Here, reference symbol $\Delta$ denotes the smallest thickness of thicknesses of the delay elements 311, 312, ..., 31N. The plane-parallel plates are arranged at preset intervals between the half mirror 2 and the first mirror 11. In the light pulse multiprocessing unit of the first aspect, as shown in FIG. 3A, there are a plurality of optical paths along which light travels from the half mirror 2 toward the first mirror 11. Each of the preset intervals is the same as an interval between adjacent optical paths of the plurality of optical paths. Specifically, the delay elements 311, 312, ..., 31N are arranged in the optical paths, one for each optical path. In the light pulse multiprocessing unit of the first aspect, the delay elements 311, 312, ..., 31N are arranged so that the thicknesses of the delay elements are gradually increased from the incidence side of the light pulse toward the emergence side. The delay elements 311, 312, ..., 31N may be arranged in random order.

Figure 3C:

According to the light pulse multiprocessing unit constructed in this way, the light pulse P emitted from a pulse light source, not shown in the figure, enters a preset place O1 on the half mirror 2. At this time, the light pulse P is split into pulses on the transmission side and the reflection side of the half mirror 2. The light pulse P transmitted through the half mirror 2 passes through the delay element 311 and changes into the light pulse $P_1$ to which the time delay is caused (FIG. 3C). The light pulse $P_1$ is reflected at a preset place A1 on the first mirror 11 and is incident on a preset place O2 on the half mirror 2. On the other hand, the light pulse P reflected by the half mirror 2 is reflected, in this state (FIG. 3B), at a preset place B1 on the second mirror 12 and is incident on a preset place O2 on the half mirror 2. Specifically, the light pulses P split at the preset place O1 on the half mirror 2 cross at the preset place O2 on the half mirror 2 through a route O1-A1-O2 and a route O1-B1-O2.

Subsequently, at the preset place O2, the light pulse $P_1$ traveling through the route O1-A1-O2 is split into pulses on the transmission side and the reflection side of the half mirror 2. Similarly, the light pulse P traveling through the route O1-B1-O2 is also split into pulses on the transmission side and the reflection side of the half mirror 2. Thus, the light pulse $P_1$ transmitted through the half mirror 2, of the light pulse $P_1$ traveling through the route O1-A1-O2, is combined, at the preset place O2, with the light pulse P reflected by the half mirror 2, of the light pulse P traveling through the route O1-B1-O2. The light pulse $P_1$ reflected by the half mirror 2, of the light pulse $P_1$ traveling through the route O1-A1-O2, is combined, at the preset place O2, with the light pulse P transmitted through the half mirror 2, of the light pulse P traveling through the route O1-B1-O2. In this way, at the preset place O2, the splitting and combination of the light pulse are performed simultaneously. Immediately after passage of light through the preset place O2, each of the split light pulses (the transmission-side light pulse and the reflection-side light pulse) includes the light pulses P and $P_1$.

Figure 3D:
Figure 3E:
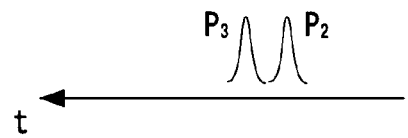
Figure 3F:
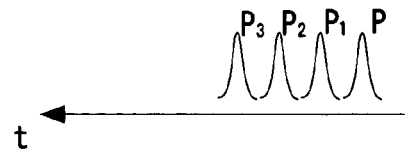

Of split light pulses, the light pulses P and $P_1$ traveling toward the first mirror 11 pass through the delay element 312. At this time, the time delay is caused and thus the light pulse P changes into the light pulse $P_2$, while the light pulse $P_1$ changes into the light pulse $P_3$ (FIG. 3E). The light pulses $P_2$ and $P_3$ are reflected at a preset A2 on the first mirror 11 and enters the preset place O3 on the half mirror 2. Of the split light pulses, the light pulses P and $P_1$ traveling toward the second mirror 12 are merely reflected at a preset place B2 on the second mirror 12, and thus the time delay is not caused. That is, the light pulses P and $P_1$ are as they are (FIG. 3D). The light pulses P and $P_1$ are incident upon the preset place O3 on the half mirror 2. Specifically, the light pulses split at the preset place O2 on the half mirror 2 cross at the preset place O3 on the half mirror 2 through a route O2-A2-O3 and a route O2-B2-O3. At the preset place O3, like the preset place O2, the splitting is carried out. Thus, as shown in FIG. 3F, each of the split light pulses includes the light pulses P, $P_1$, $P_2$, and $P_3$.

In the light pulse multiprocessing unit of the first aspect, as mentioned above, the reflection and the splitting-combination are alternately repeated with respect to transmitted light produced when the light pulse is initially split, in the process that the light follows an optical path O1-A1-O2-B2-O3. Similarly, the reflection and the splitting-combination are alternately repeated with respect to reflected light produced when the light pulse is initially split, in an optical path O1-B1-O2-A2-O3.

Specifically, in the light pulse multiprocessing unit of the first aspect, for example, from the preset place O1 on the half mirror 2 to the preset place O3, there are four routes:
(1) O1-A1-O2-A2-O3
(2) O1-A1-O2-B2-O3
(3) O1-B1-O2-A2-O3
(4) O1-B1-O2-B2-O3

In FIG. 3A, the light pulses following the four routes are combined simultaneously at the preset place O3 on the half mirror 2. At this time, in the absence of the delay elements 311 and 322, it can easily be understood that a combined light pulse includes only the light pulse P. In the light pulse multiprocessing unit of the first aspect, by contrast, the delay elements 311 and 312 are constructed with plane-parallel plates using glass materials of the same refractive index n and have thicknesses of $\Delta$ and $2\Delta$, respectively. The optical path length of the light pulse inside the delay element is obtained by multiplying a refractive index n−1 by the thickness. Thus, the optical path difference in each route varies as described below. As a result, the light pulse following each route, upon reaching the preset place O3 on the half mirror 2, produces a time difference (time delay).

| Route | Optical path difference |
|---|---|
| O1-A1-O2-A2-O3 | $3\Delta(n-1)$ |
| O1-A1-O2-B2-O3 | $1\Delta(n-1)$ |
| O1-B1-O2-A2-O3 | $2\Delta(n-1)$ |
| O1-B1-O2-B2-O3 | $0\Delta(n-1)$ |

That is, the light pulses following the four routes changes to the light pulse train that has a pulse interval of $\Delta(n-1)/C$, where C is a light velocity. In routes along which the light pulse reaches a preset place ON +1 on the half mirror 2, located behind the above routes, the light pulse, as in the above routes, repeats the splitting and combination N times. Whereby, according to the light pulse multiprocessing unit of the first aspect, $2^N$ pulse trains can be produced. Moreover, in the pulse trains produced in the light pulse multi-processing unit of the first aspect, the light pulses are not spatially separated, but propagate completely along the same axis. Consequently, even though the light pulse trains multi-processed through the light pulse multiprocessing unit of the first aspect are collected by means of the condenser lens, all light pulses are collected at the same point from the same direction and thus, when a connection with a optical fiber is attempted, favorable connection efficiency can be realized.

Description of the Second Aspect

Figure 4:
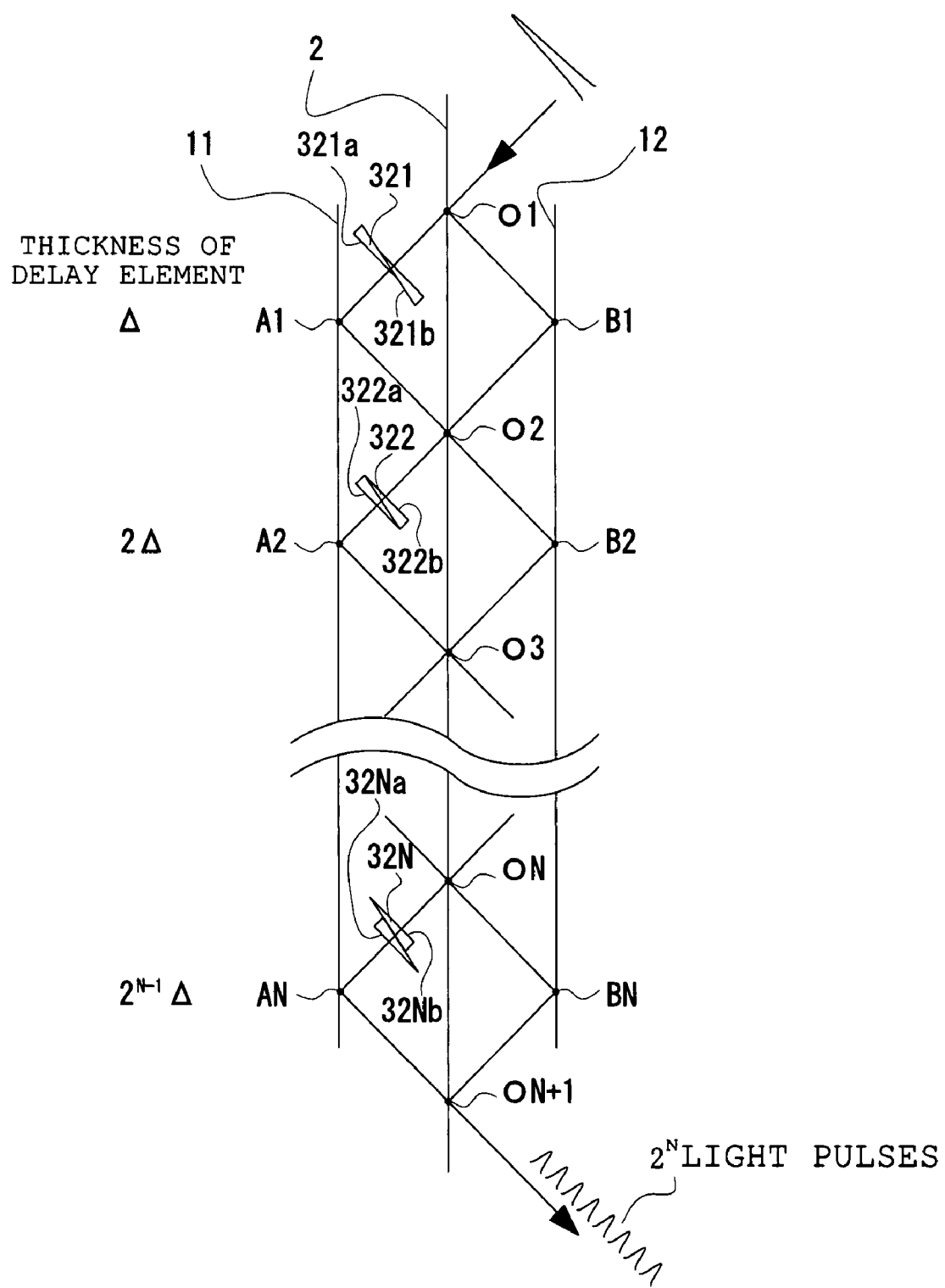
FIG. 4 is a view showing a schematic structure of the light pulse multiprocessing unit of a second aspect in the present invention.

FIG. 4 shows the light pulse multiprocessing unit of the second aspect in the present invention.

In the light pulse multiprocessing unit of the first aspect, the plane parallel plate that is constant in thickness is used as each delay element, and hence the pulse intervals of the light pulse train are fixed. In contrast to this, in the light pulse multiprocessing unit of the second aspect, delay elements 321, 322, . . . , 32N that are variable in thickness are used instead of the delay elements 311, 312, . . . , 31N shown in FIG. 3A. Whereby, in the light pulse multiprocessing unit of the second aspect, the pulse intervals of the light pulse train are made variable.

In the light pulse multiprocessing unit of the second aspect, as shown in FIG. 4, the individual delay elements 321, 322, . . . , 32N include a pair of wedge prisms 321a and 321b, a pair of wedge prisms 322a and 322b, . . . , a pair of wedge prisms 32Na and 32Nb, respectively.

The pairs of wedge prisms 321a and 321b; 322a and 322b; . . . ; 32Na and 32Nb are such that surfaces of each pair of wedge prisms come in contact with each other to constitute a prism unit. The prism unit is constructed so that two wedge prisms are relatively moved in parallel along a contact plane (corresponding to one of the prism surfaces making the smallest apex angle). This movement may be conducted by one of the two wedge prisms or by both. Thus, in the light pulse multiprocessing unit of the second aspect, the two wedge prisms are moved. Whereby, a thickness $\Delta'$ of the delay element can be varied in accordance with overlapping of the pair of wedge prisms. Consequently, according to the light pulse multiprocessing unit of the second aspect, it becomes possible to arbitrarily change the pulse intervals of the light pulse train. Other structure, functions, and effects are almost the same as in the light pulse multiprocessing unit of the first aspect.

Description of the Third Aspect

Figure 5:
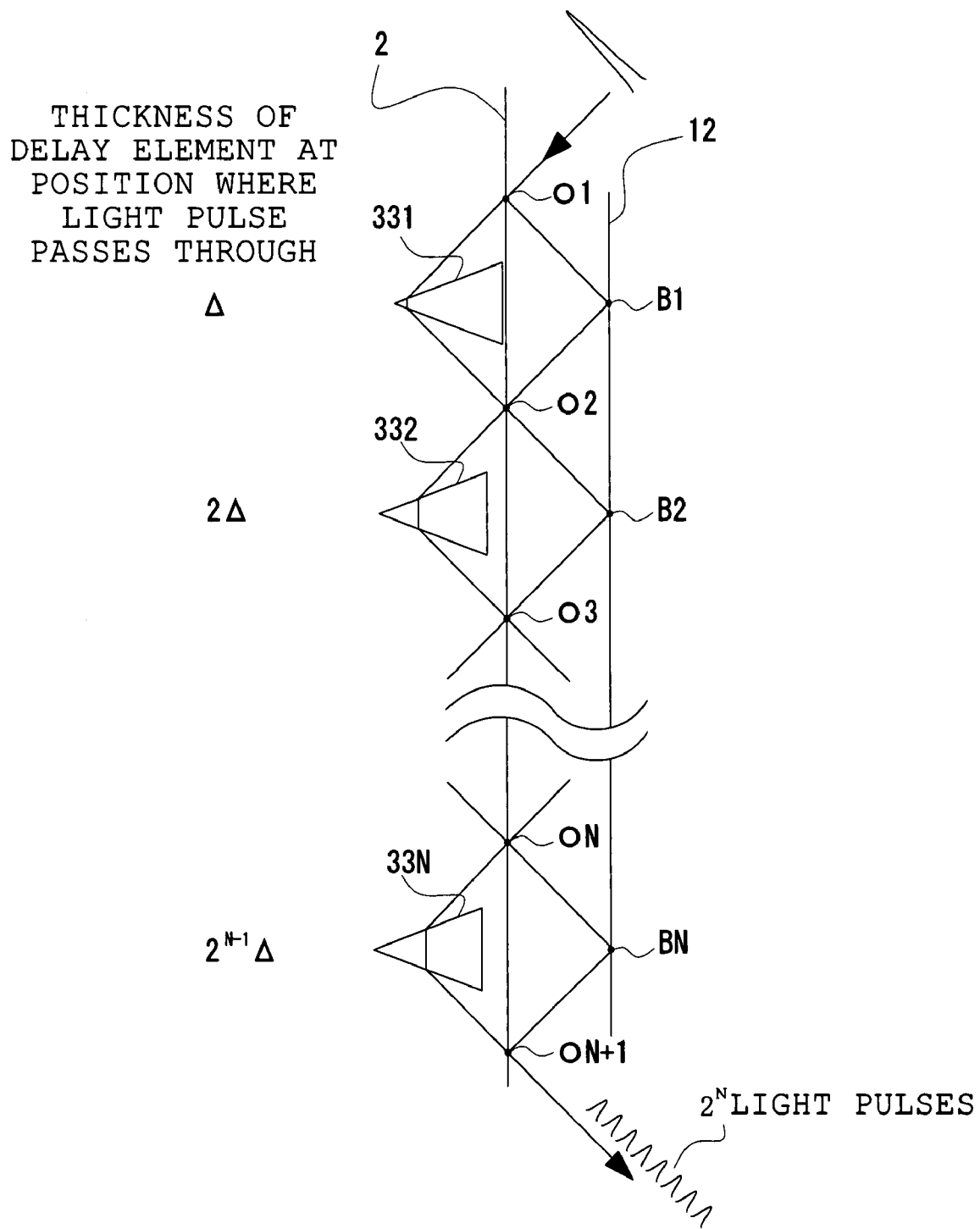
FIG. 5 is a view showing a schematic structure of the light pulse multiprocessing unit of a third aspect in the present invention.
Figure 6A:
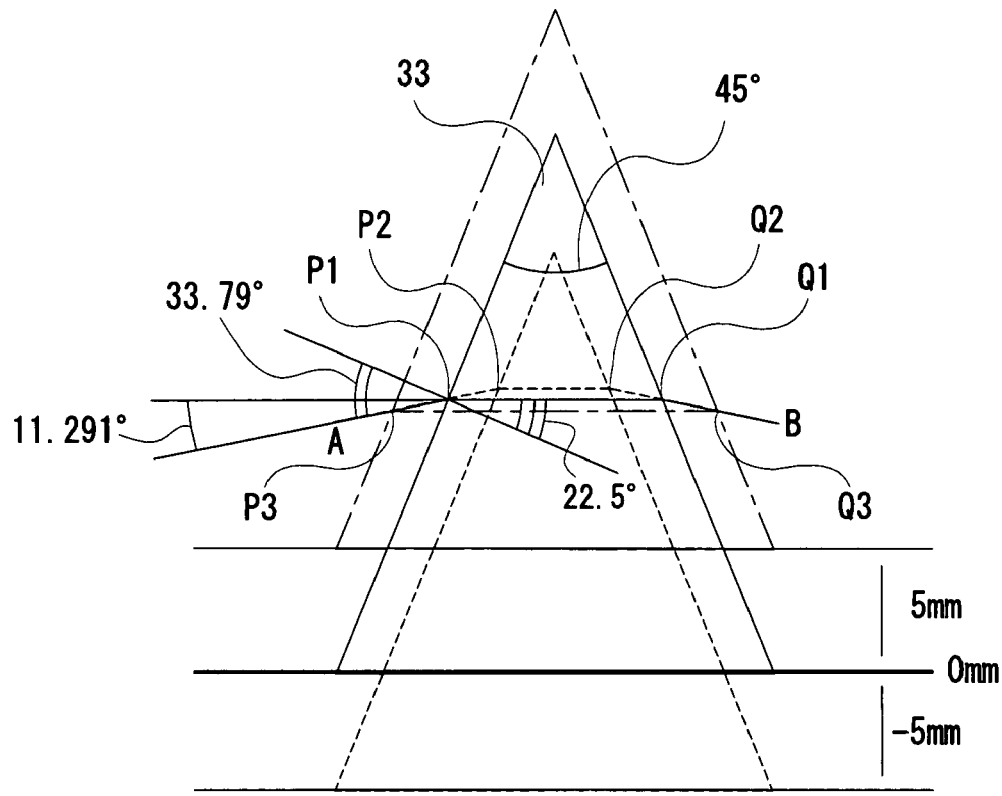
FIGS. 6A and 6B are explanatory views showing one structural example of a delay element used in the light pulse multiprocessing unit of the third aspect and variation of the optical path length where the position of the delay element is changed.
Figure 6B:
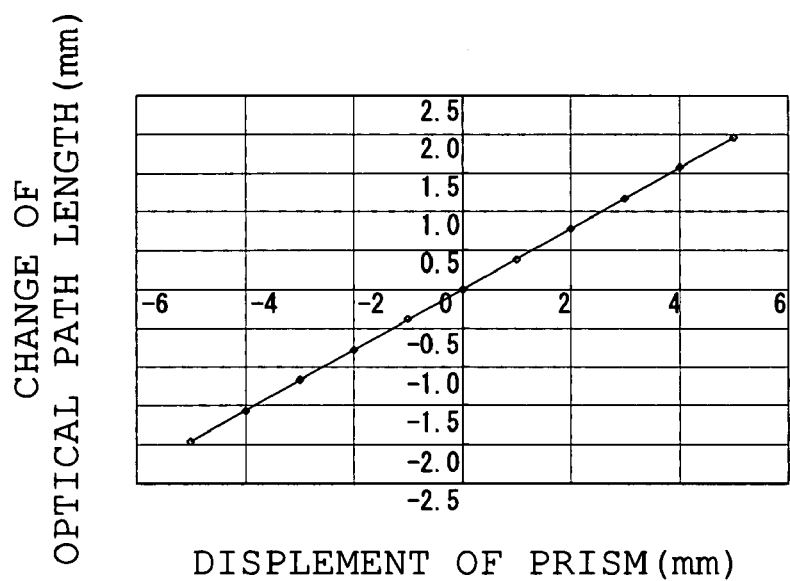

FIG. 5 shows the light pulse multiprocessing unit of the third aspect in the present invention. FIGS. 6A and 6B show one structural example of a delay element used in the light pulse multiprocessing unit of the third aspect and variation of the optical path length where the position of the delay element is changed. Specifically, FIG. 6A is an explanatory view showing its state and FIG. 6B is a graph showing the change of the optical path length against the displacement of the prism constituting the delay element of FIG. 6A.

The light pulse multiprocessing unit of the third aspect includes the mirror 12, the half mirror 2, and N delay elements 331, 332, . . . , 33N, each having the refractive index n. The half mirror 2 is placed parallel to the mirror 12.

The N delay elements 331, 332, . . . , 33N are constructed with wedge prisms of identical shape, configured using glass materials of the same refractive index n. The individual wedge prisms are arranged on the opposite side of the mirror 12 with respect to the half mirror 2. In this case, each of the wedge prisms is placed so that a surface subtending the apex angle of the wedge prism is located on the half-mirror-2 side. That is, each wedge prism is placed so that the apex angle is far away from the half mirror 2.

The individual wedge prisms are also arranged so that distances from the surfaces subtending the apex angles to the half mirror 2 are different from one another. The wedge prisms are further arranged so as to satisfy the minimum deflection angle with respect to each of the light pulses transmitted through the half mirror 2.

When the light pulse is rendered obliquely incident on the half mirror 2, the half mirror 2 splits the light pulse into a reflection-side pulse and a transmission-side pulse. One of the light pulses that have been split is reflected at the mirror 12. The other light pulse is deflected by refractive functions of the wedge prisms constituting the delay elements 331, 332, . . . , 33N. After that, the deflected light pulses are combined at a common place on the half mirror 2. The combined light pulse is split again by the half mirror 2. In this way, in the light pulse multiprocessing unit of the third aspect, the operation ranging from the splitting of the light pulse by the half mirror 2 to the combination of the light pulses on the half mirror 2 is repeated N times. The half mirror 2, the mirror 12, and the wedge prisms 331, 332, . . . , 33N have predetermined sizes so that the splitting and combination are performed a plurality of times. The light pulse multiprocessing unit thus constructed is arranged and used so that the half mirror 2 and the mirror 12 are inclined with respect to the incident optical path of the light pulse.

Even in the light pulse multiprocessing unit of the third aspect, the splitting of the light pulse by the half mirror 2 and the combination of the light pulses on the half mirror 2 are repeated N times. In one optical path in which the operation ranging from the splitting to the combination is performed, one delay element is placed. Hence, the N delay elements 331, 332, . . . , 33N are arranged, one for each optical path, so as to satisfy the optical path differences of $(n-1)\Delta$, $2(n-1)\Delta$, . . . , $2^{N-1}(n-1)\Delta$, respectively.

In the light pulse multiprocessing unit of the third aspect, as mentioned above, refraction, splitting-combination, and reflection are performed in preset order in the process that transmitted light produced when light is initially split follows an optical path O1-the wedge prism 331-O2-B2-O3. In the case of FIG. 5, this preset order includes the order of operations: refraction, splitting-combination, reflection, splitting-combination, and refraction. Likewise, in the process that reflected light produced when the light is initially split follows an optical path O1-B1-O2-the wedge prism 332-O3, refraction, splitting-combination, and reflection are performed in preset order. In the case of FIG. 5, this preset order includes the order of operations: reflection, splitting-combination, refraction, splitting-combination, and reflection.

The delay elements 331, 332, . . . , 33N constructed with the wedge prisms functions as delay elements and also as deflection elements. In the light pulse multiprocessing unit of the third aspect, therefore, there is no need to provide the first mirror required for the light pulse multiprocessing unit in each of the first and second aspects.

Using FIGS. 6A and 6B, the function of the delay elements 331, 332, . . . , 33N will be described in detail below. Also, in the light pulse multiprocessing unit of the third aspect, the delay elements 331, 332, . . . , 33N are the same in structure. Hence, in FIG. 6A, one of the delay elements 331, 332, . . . , 33N is shown as a delay element (a prism or wedge prism) 33.

In the delay element 33 shown in FIG. 6A, synthetic quartz is used as the glass material. The delay element 33 is configured into the shape of an isosceles triangle whose apex angle is 45°. In the light pulse multiprocessing unit of the third aspect using the prism 33, a light pulse with a wavelength of 800 nm is to be incident.

In this case, the prism 33 is placed so as to satisfy the minimum deflection angle. Specifically, the prism 33 is placed so that the bottom surface of the prism 33 becomes parallel to the half mirror 2. Furthermore, the prism 33 is placed so that when the light pulse is incident on the prism 33, an angle made by the incident ray of the light pulse with a line L1 parallel to the half mirror 2 (namely, horizontally on the plane of the page) is 11.291°. In this case, the angle of incidence of the light pulse made with the normal line of the plane of incidence on the prism 33 is 33.79°, and the angle of refraction of the light pulse refracted by the prism 33 is 22.5°.

The delay element 33 thus constructed with the wedge prism, as shown in FIG. 6A, is shifted vertically (namely, in a direction perpendicular to the half mirror 2) on the plane of the page. At this time, a position (positions P1~P3) of the delay element 33 on which the light pulse is incident, an optical path length from the transmission of the light pulse through the half mirror 2 to the incidence of the light pulse on the delay element 33, a route (routes P1-Q1~P3-Q3) along which the light pulse incident on the delay element 33 travels parallel to the half mirror 2 (namely, horizontally on the plane of the page) and its length, a position (positions Q1~Q3) of the delay element 33 from which the light pulse emerges, and an optical path length ranging from the emergence of the light pulse from the delay element 33 to the re-incidence of the light pulse on the half mirror 2 are changed. In the delay element 33, however, the angle of the incident ray of the light pulse and the angle of the emergent ray are not entirely changed. In FIG. 6A, when the preset position is taken as a reference position, a route where the preset position is shifted downward (that is, perpendicular and close to the half mirror 2) by −5 mm from the reference position on the plane of the page is indicated by a dotted line, a rout where the displacement of the preset position is 0 mm with respect to the reference position by a solid line, and a route where the preset position is shifted upward (that is, perpendicular to and far away from the half mirror 2) by +5 mm from the reference position on the plane of the page by a chain line.

The delay element 33 constructed with this wedge prism, as shown in FIG. 6A, is now moved by ±5 mm with respect to the reference position. In this case, the amount of change of the optical path length of the light pulse directed from a direction A through the delay element 33 toward a direction B is as shown in FIG. 6B. In the graph of FIG. 6B, however, the optical path length where the amount of change of the delay element 33 relative to the preset reference position is 0 mm is taken as a reference and the difference with the optical path length is shown.

As will be clear from FIGS. 6A and 6B, even when the delay element 33 is shifted vertically (namely, in a direction perpendicular to the half mirror 2) on the plane of the page, the angles of the incident ray and the emergent ray of the light pulse relative to the delay element 33 are not entirely changed. On the other hand, the thickness of the delay element 33 at the position where the light pulse passes through, as in the light pulse multi-processing unit of the first aspect, changes to $\Delta, 2\Delta, \ldots, 2^{N-1}\Delta$. Consequently, it is found that optical path differences in individual routes from the preset place O1 on the half mirror 2 to a preset place ON+1 are changed even in the light pulse multiprocessing unit of the third aspect. That is, in the light pulse multiprocessing unit shown in FIG. 5, distances from the individual delay elements 331, 332, . . . , 33N to the half mirror 2 are changed. Whereby, like the light pulse multiprocessing unit in each of the first and second aspects, the light pulse train can be produced even in the light pulse multiprocessing unit of the third aspect. In addition, like the light pulse multiprocessing unit of the second aspect, the pulse intervals of the light pulse train can be arbitrarily changed.

Description of the Fourth Aspect

Figure 7:
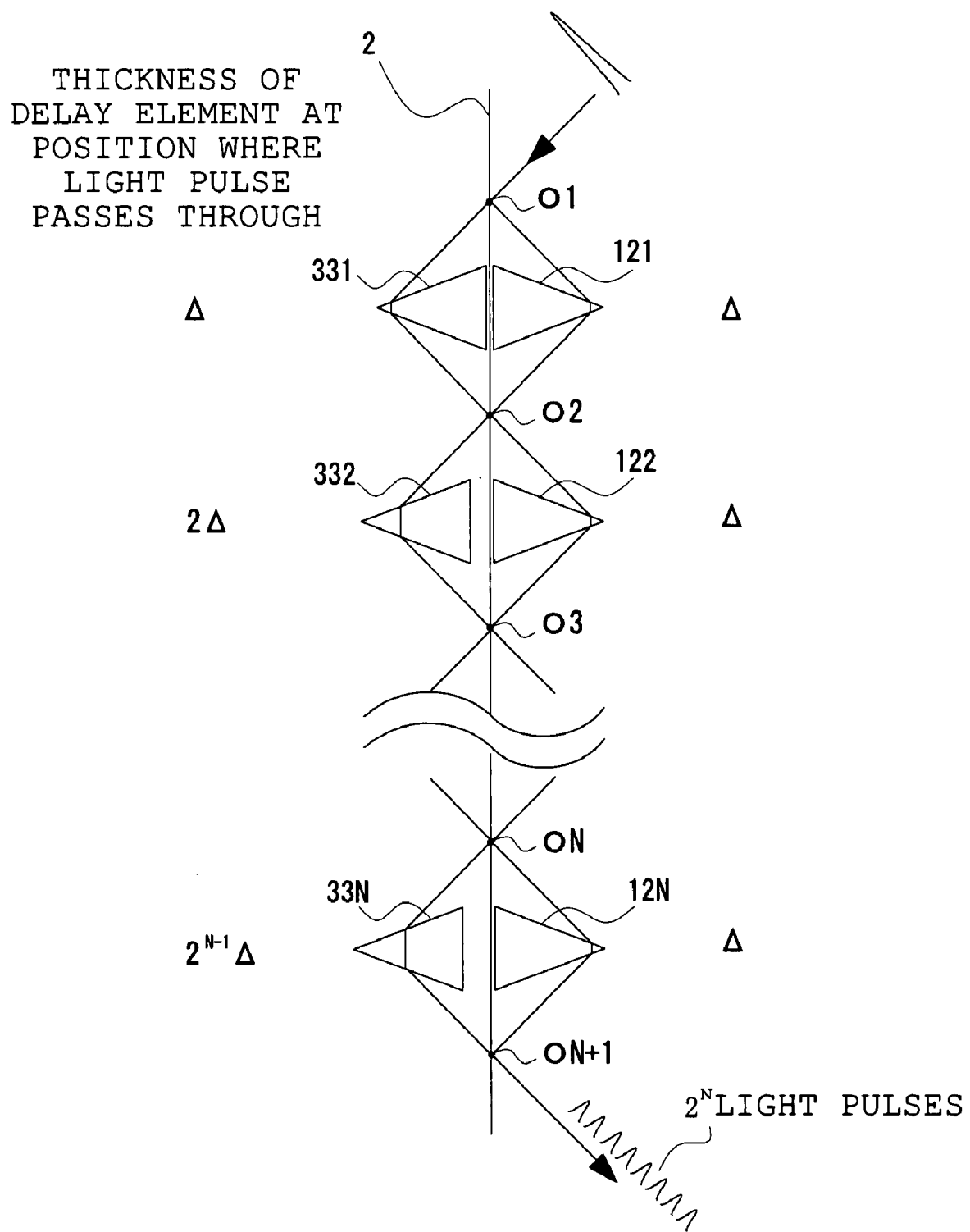
FIG. 7 is a view showing a schematic structure of the light pulse multiprocessing unit of a fourth aspect in the present invention.

FIG. 7 shows the light pulse multiprocessing unit of the fourth aspect in the present invention.

The light pulse multiprocessing unit of the fourth aspect, instead of using the mirror 12 in the light pulse multiprocessing unit of the third aspect shown in FIG. 5, uses N delay elements 121, 122, . . . , 12N constructed with the wedge prisms like the N delay elements 331, 332, . . . , 33N.

The N delay elements 121, 122, . . . , 12N are arranged opposite to the N delay elements 331, 332, . . . , 33N, with respect to the half mirror 2. The N delay elements 121, 122, . . . , 12N are arranged so as to satisfy the minimum angle of deflection in reference to the light pulse transmitted through, and reflected by, the half mirror 2. Further, the N delay elements 121, 122, . . . , 12N are such as to deflect an incident light pulse to emerge toward the half mirror 2.

In the light pulse multiprocessing unit of the fourth aspect, the refraction and the splitting-combination are alternately repeated with respect to transmitted light produced when the light pulse is initially split, in the process that the light follows an optical path O1-the prism 331-O2-the prism 122-O3. Similarly, the refraction and the splitting-combination are alternately repeated with respect to reflected light produced when the light pulse is initially split, in the process that the light follows an optical path O1-the prism 121-O2-the prism 332-O3.

The half mirror 2 splits the light pulse into a reflection-side pulse and a transmission-side pulse when the light pulse is rendered obliquely incident on the half mirror 2. Individual light pulses that have been split are deflected by refractive functions of the wedge prisms constituting the delay elements located on corresponding sides. The light pulses that have been deflected are combined at a common place on the half mirror 2. Thus, in the light pulse multiprocessing unit of the fourth aspect, the operation ranging from the splitting of the light pulse by the half mirror 2 to the combination of the light pulses on the half mirror 2 is repeated N times. The half mirror 2, the N delay elements 331, 332, . . . , 33N, and the N delay elements 121, 122, . . . , 12N have predetermined sizes so that the splitting and combination are performed a plurality of times. The light pulse multiprocessing unit thus constructed is arranged and used so that the half mirror 2 is inclined with respect to the incident optical path of the light pulse.

However, the N delay elements 121, 122, ..., 12N are different from the N delay elements 331, 332, ..., 33N and are not arranged so that the amount of delay is changed. In other words, the N delay elements 121, 122, ..., 12N are arranged so that all distances from the half mirror 2 become equal. Whereby, the N delay elements 121, 122, ..., 12N function like the mirror 12 in the light pulse multiprocessing unit of the third aspect.

According to the light pulse multiprocessing unit of the fourth aspect, the same effect as in the light pulse multiprocessing unit of the third aspect is attained.

Description of the Fifth Aspect

Figure 8A:
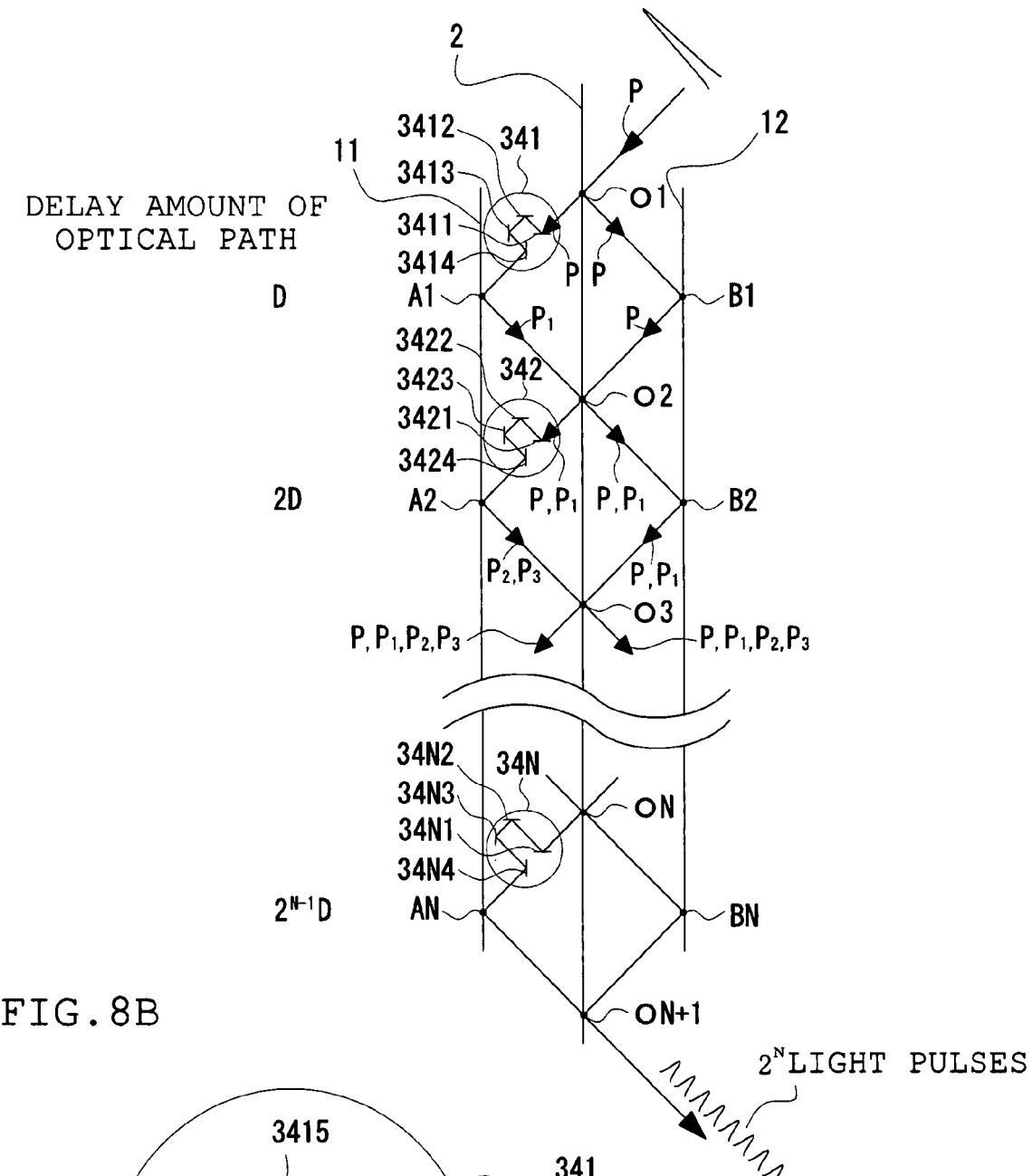
FIGS. 8A and 8B are views showing a schematic structure of the light pulse multiprocessing unit of a fifth aspect in the present invention.
Figure 8B:
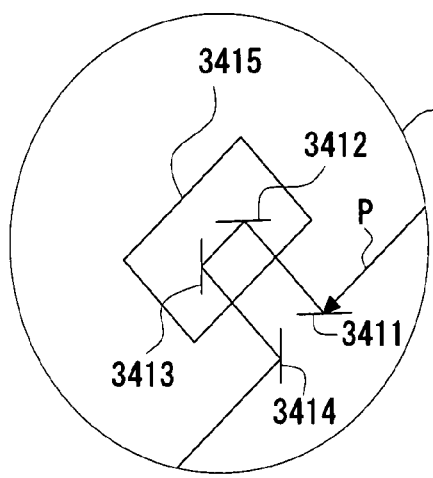

FIGS. 8A and 8B show the light pulse multiprocessing unit of the fifth aspect in the present invention. FIG. 8A is a general view and FIG. 8B is an enlarged view of a first delay means (a part surrounded by a circle) in FIG. 8A. The light pulse multiprocessing unit of the fifth aspect, instead of using the delay elements 321, 322, ..., 32N combined by the pairs of wedge prisms in the second aspect, uses a combination of four-mirror units 341, 342, ..., 34N so that the intervals of the light pulse train are made variable.

That is, in the fifth aspect, the mirror unit 341 as the first delay means, as illustrated in FIGS. 8A and 8B, is provided with mirrors 3411, 3412, 3413, and 3414, each of which deflects light in a perpendicular direction. The mirrors 3412 and 3413 are fixed integrally with a mirror moving unit 3415, which is such that an opposite interval is variable with respect to the mirrors 3411 and 3414.

The mirror unit 342 as a second delay means, ..., the mirror unit 34N as an Nth delay means are likewise constructed, and individual optical path lengths are properly adjusted by the mirror moving unit 3415 so that when the optical path difference caused by the mirror unit 341 is denoted by D, the optical path difference by the mirror unit 34N becomes $2^{N-1}\,^1D$.

Other structures, functions, and effects are nearly the same as in the light pulse multi-processing unit of each of the first and second aspects.

In accordance with the drawings, the structures of embodiments in the present invention will be described below.

Embodiment 1

Figure 9:
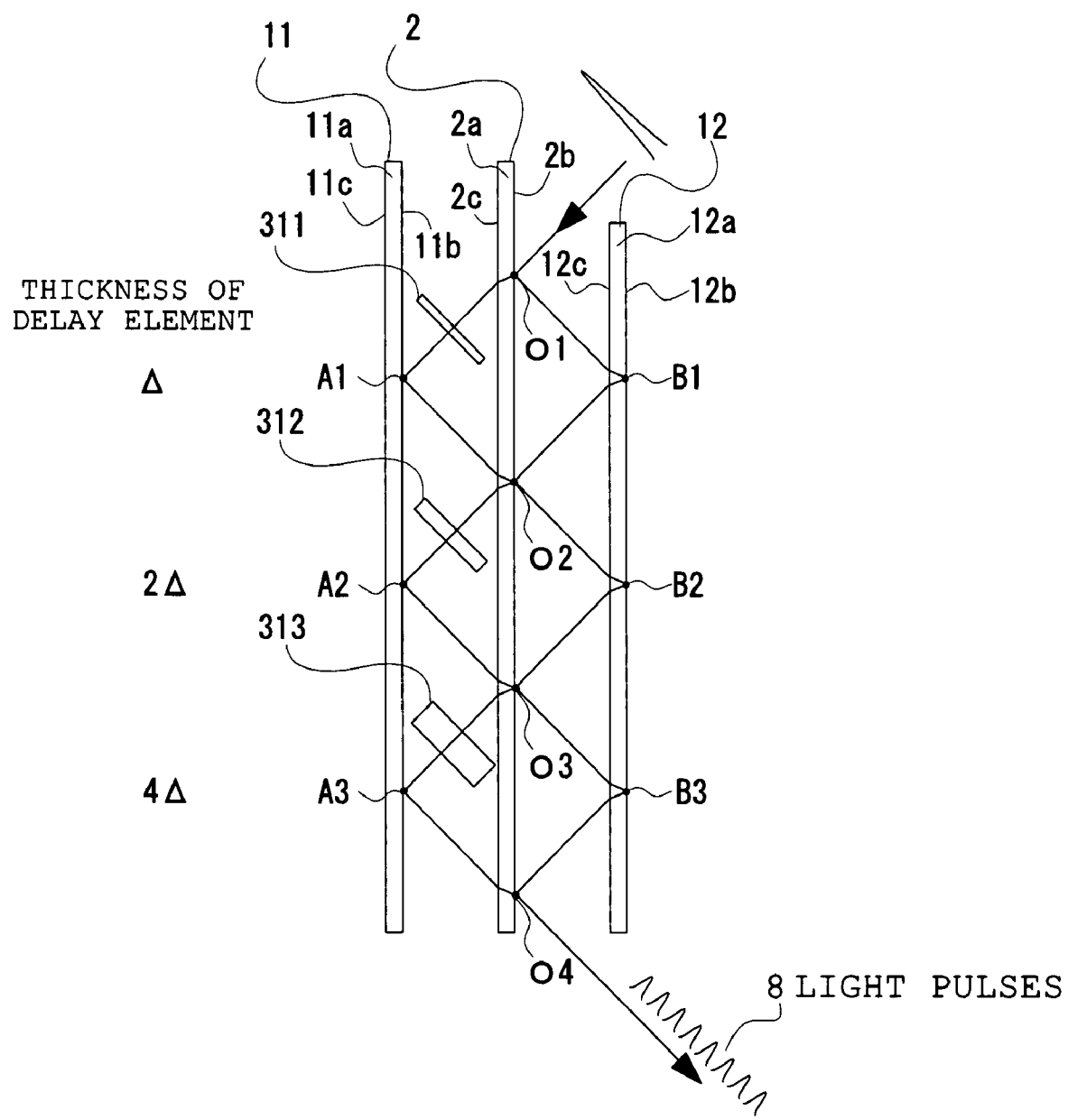
FIG. 9 is a view showing a schematic structure of the light pulse multiprocessing unit of Embodiment 1 in the present invention.

FIG. 9 shows the light pulse multiprocessing unit of Embodiment 1 in the present invention.

The light pulse multiprocessing unit of Embodiment 1 specifies the structure of the light pulse multiprocessing unit of the first aspect shown in FIG. 3A and includes the first mirror 11, the second mirror 12, the half mirror 2, and three delay elements 311, 312, and 313, each having the refractive index n.

The half mirror 2 is provided with a semi-transmissive reflecting film on one surface 2b of a plane-parallel plate 2a having predetermined thickness. The second mirror 12 has a plane-parallel plate 12a of the same thickness as the plane-parallel plate 2a. The mirror 12 is provided with a reflecting film on a surface 12b, lying on the opposite side of a half-mirror-2-side surface 12c, of two surfaces of the plane-parallel plate 12a. The first mirror 11 has a plane-parallel plate 11a. The first mirror 11 is provided with a reflecting film on a half-mirror-2-side surface 11b, of two surfaces of the plane-parallel plate 11a.

When an arrangement of the semi-transmissive reflecting film of the half mirror 2 and the reflecting films of the two mirrors 11 and 12 and the thicknesses of the plane-parallel plates are designed as mentioned above, the optical path lengths of light pulses split through the half mirror 2 can be made equal even when the light pulses follow any routes, so that the light pulses can be combined at the common place on the half mirror 2.

The first mirror 11 and the second mirror 12 are arranged parallel and opposite to each other.

The half mirror 2 is placed parallel to the first mirror 11 and the second mirror 12 in the proximity of an intermediate position between the first mirror 11 and the second mirror 12. The half mirror 2 splits the light pulse into a reflection-side pulse and a transmission-side pulse when the light pulse is rendered obliquely incident on the half mirror 2. One of the light pulses that have been split is reflected at the first mirror 11. The other light pulse is reflected at the second mirror 12. Light reflected by the first mirror 11 and the second mirror 12 is combined at the common place on the half mirror 2. The light pulse that has been combined is split again by the half mirror 2. In this way, in the light pulse multiprocessing unit of Embodiment 1, the operation ranging from the splitting of the light pulse by the half mirror 2 to the combination of the light pulses on the half mirror 2 is repeated three times. The first mirror 11, the second mirror 12, and the half mirror 2 have predetermined sizes so that the splitting and combination can be performed a plurality of times. The light pulse multiprocessing unit constructed as mentioned above is arranged and used so that the first mirror 11, the second mirror 12, and half mirror 2 are inclined with respect to the incident optical path of the light pulse.

The three delay elements 311, 312, and 313 are constructed with plane-parallel plates. Individual plane-parallel plates use glass materials of the same refractive index n. The plane-parallel plates have thicknesses of Δ, 2Δ, and 4Δ, respectively. The plane-parallel plates are arranged at preset intervals between the half mirror 2 and the first mirror 11. In the light pulse multiprocessing unit of Embodiment 1, as shown in FIG. 9, there are three optical paths along which light travels from the half mirror 2 toward the first mirror 11. Each of the preset intervals is the same as an interval between adjacent optical paths of the plurality of optical paths. Specifically, the delay elements 311, 312, and 313 are arranged in the optical paths, one for each optical path. In the light pulse multiprocessing unit of Embodiment 1, the delay elements 311, 312, and 313 are arranged so that the thicknesses of the delay elements are gradually increased from the incidence side of the light pulse toward the emergence side.

Other structures, functions, and effects are the same as in the light pulse multiprocessing unit of the first aspect. Also, although in the light pulse multiprocessing unit of Embodiment 1 the three delay elements are arranged, more delay element can, of course, be arranged to construct the light pulse multiprocessing unit.

Embodiment 2

Figure 10:
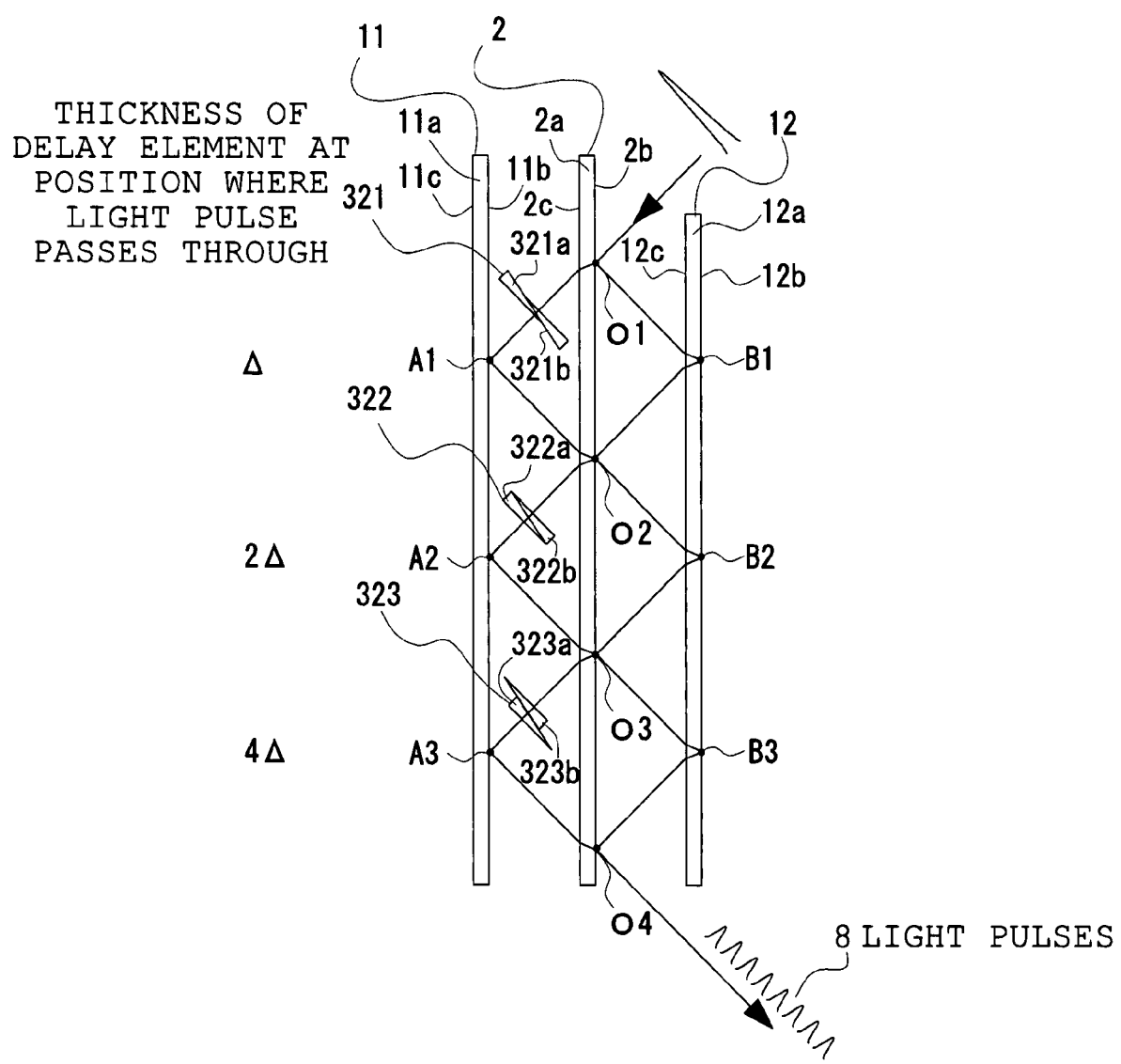
FIG. 10 is a view showing a schematic structure of the light pulse multiprocessing unit of Embodiment 2 in the present invention.

FIG. 10 shows the light pulse multiprocessing unit of Embodiment 2 in the present invention.

The light pulse multiprocessing unit of Embodiment 2 specifies the structure of the light pulse multiprocessing unit of the second aspect shown in FIG. 4. Specifically, instead of the delay elements 311, 312, and 313 in the light pulse multiprocessing unit of Embodiment 1 shown in FIG. 9, the delay elements 321, 322, and 323 that are variable in thickness are used so that the pulse internals of the light pulse train can be changed. Individual delay elements 321, 322, and 323 include a pair of wedge prisms 321a and 321b, a pair of wedge prisms 322a and 322b, and a pair of wedge prisms 323a and 323b, respectively.

The pairs of wedge prisms 321a and 321b, 322a and 322b, and 323a and 323b are such that surfaces of each pair of wedge prisms come in contact with each other to constitute a prism unit. The prism unit is constructed so that two wedge prisms can be moved in parallel along their contact plane. In accordance with overlapping of the pair of wedge prisms, the thickness Δ' of the delay element can be varied. Consequently, according to the light pulse multiprocessing unit of Embodiment 2, it becomes possible to arbitrarily change the pulse intervals of the light pulse train.

Other structures, functions, and effects are nearly the same as in the light pulse multi-processing unit of Embodiment 1. Also, although in the light pulse multiprocessing unit of Embodiment 2 the three delay elements are arranged, more delay element can, of course, be arranged to construct the light pulse multiprocessing unit.

Embodiment 3

Figure 11:
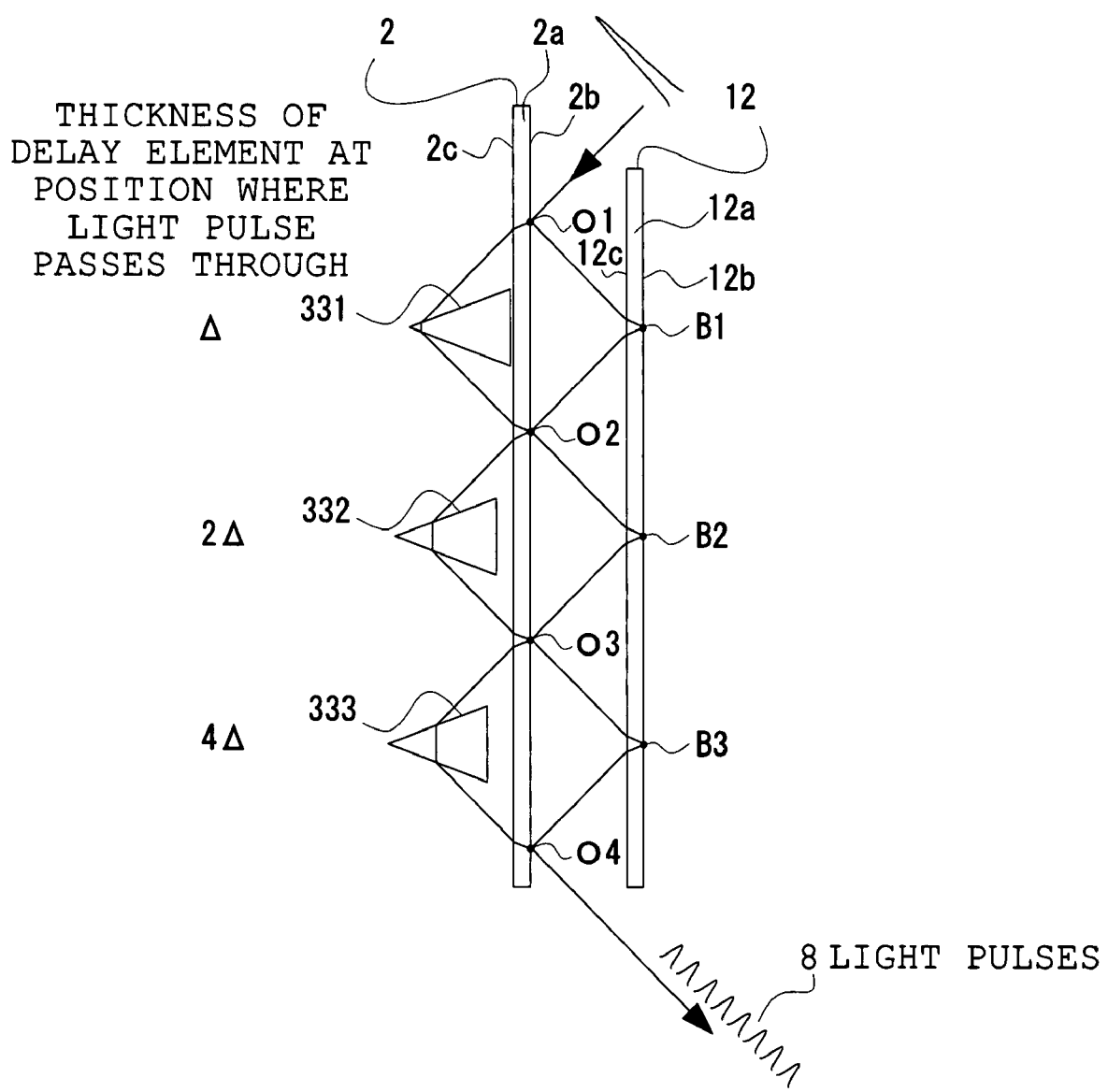
FIG. 11 is a view showing a schematic structure of the light pulse multiprocessing unit of Embodiment 3 in the present invention.

FIG. 11 shows the light pulse multiprocessing unit of Embodiment 3 in the present invention. The light pulse multiprocessing unit of Embodiment 3 specifies the structure of the light pulse multiprocessing unit of the third aspect shown in FIGS. 5, 6A, and 6B and includes the mirror 12, the half mirror 2, and three delay elements 331, 332, and 333, each having the refractive index n.

The half mirror 2 is provided with a semi-transmissive reflecting film on one surface 2a of the plane-parallel plate 2a having predetermined thickness. The mirror 12 has the plane-parallel plate 12a of the same thickness as the plane-parallel plate 2a. The mirror 12 is provided with a reflecting film on the surface 12b, lying on the opposite side of the half-mirror-2-side surface 12c, of two surfaces of the plane-parallel plate 12a.

When an arrangement of the semi-transmissive reflecting film of the half mirror 2 and 20 the reflecting film of the mirror 12 and the thicknesses of the plane-parallel plates are designed as mentioned above, the optical path lengths of light pulses split through the half mirror 2 can be made equal even when the light pulses follow any routes, so that the light pulses can be combined at the common place on the half mirror 2. The half mirror 2 is placed parallel to the mirror 12.

The three delay elements 331, 332, and 333 are constructed with wedge prisms of identical shape, configured using glass materials of the same refractive index n. The individual wedge prisms are arranged on the opposite side of the mirror 12 with respect to the half mirror 2. The wedge prisms are arranged so as to satisfy the minimum deflection angle with respect to each of the light pulses transmitted through the half mirror 2. When the light pulse is rendered obliquely incident on the half mirror 2, the half mirror 2 splits the light pulse into a reflection-side pulse and a transmission-side pulse. One of the light pulses that have been split is reflected at the mirror 12. The other light pulse is deflected by refractive functions of the wedge prisms constituting the delay elements 331, 332, and 333. After that, the deflected light pulses are combined at the common place on the half mirror 2. The combined light pulse is split again by the half mirror 2. In this way, in the light pulse multiprocessing unit of Embodiment 3, the operation ranging from the splitting of the light pulse by the half mirror to the combination of the light pulses on the half mirror 2 is repeated three times. The half mirror 2, the mirror 12, and the wedge prisms 331, 332, and 333 have predetermined sizes so that the splitting and combination are performed a plurality of times. The light pulse multiprocessing unit thus constructed is arranged and used so that the half mirror 2 and the mirror 12 are inclined with respect to the incident optical path of the light pulse.

Even in the light pulse multiprocessing unit of Embodiment 3, the splitting of the light pulse by the half mirror 2 and the combination of the light pulses on the half mirror 2 are repeated three times. In one optical path in which the operation ranging from the splitting to the combination is performed, one delay element is placed. Hence, the three delay elements 331, 332, and 333 are arranged, one for each optical path, so as to satisfy the optical path differences of (n−1)Δ, 2(n−1)Δ, and 4(n−1)Δ, respectively.

Other structures, functions, and effects are nearly the same as in the light pulse multi-processing unit of the third aspect. Also, although in the light pulse multiprocessing unit of Embodiment 3 the three delay elements are arranged, more delay element can, of course, be arranged to construct the light pulse multiprocessing unit.

Embodiment 4

Figure 12:
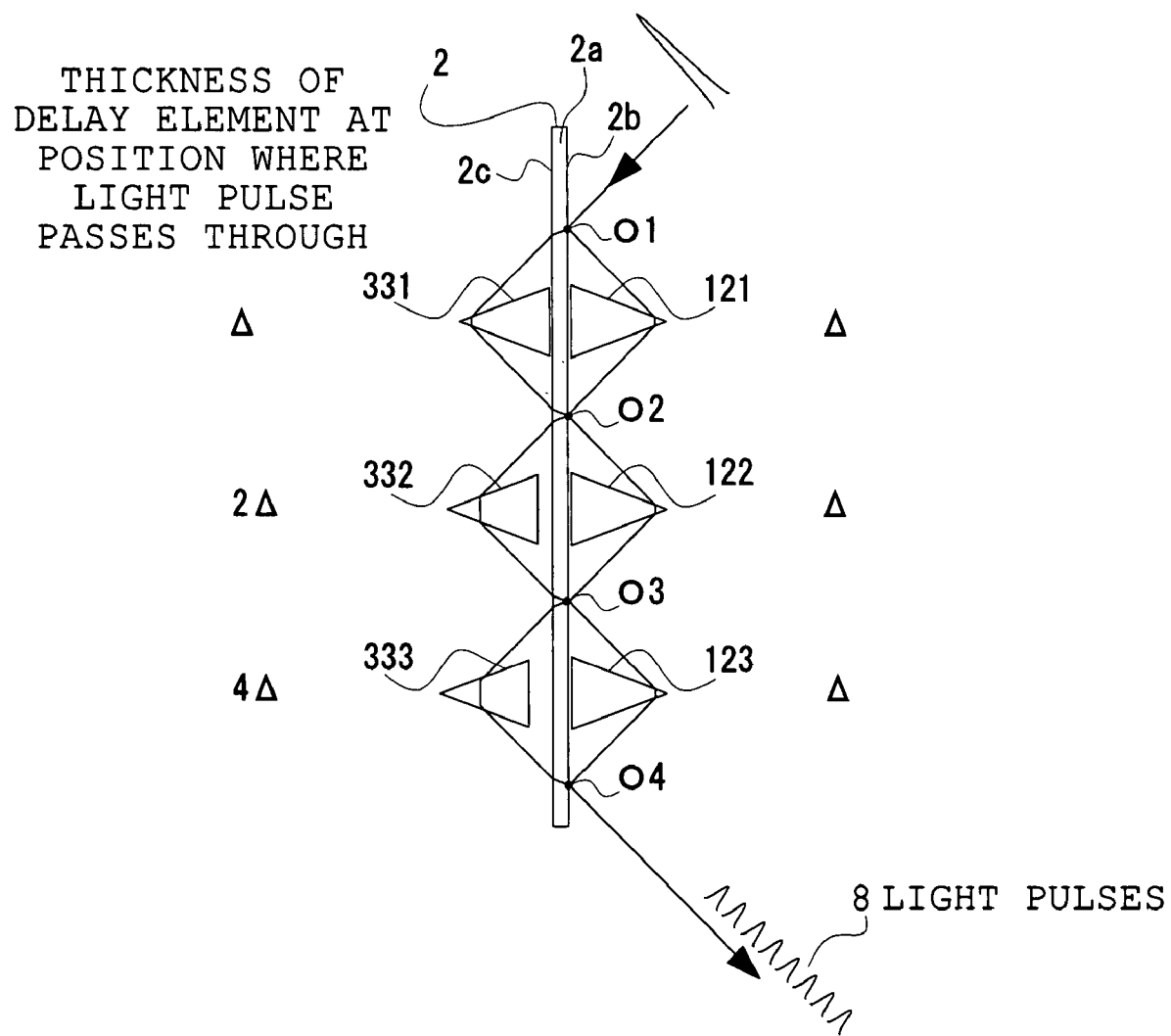
FIG. 12 is a view showing a schematic structure of the light pulse multiprocessing unit of Embodiment 4 in the present invention.

FIG. 12 shows the light pulse multiprocessing unit of Embodiment 4 in the present invention. The light pulse multiprocessing unit of Embodiment 4 specifies the structure of the light pulse multiprocessing unit of the fourth aspect shown in FIG. 7 and, instead of using the mirror 12 in the light pulse multiprocessing unit of Embodiment 3 shown in FIG. 11, uses three delay elements 121, 122, and 123 constructed with the wedge prisms like the three delay elements 331, 332, and 333.

The three delay elements 121, 122, and 123 are arranged opposite to the three delay elements 331, 332, and 333, with respect to the half mirror 2. The three delay elements 121, 122, and 123 are also arranged so as to satisfy the minimum angle of deflection with respect to the light pulse transmitted through, and reflected by, the half mirror 2. Further, the three delay elements 121, 122, and 123 are such as to deflect an incident light pulse to emerge toward the half mirror 2.

The half mirror 2 splits the light pulse into a reflection-side pulse and a transmission-side pulse when the light pulse is rendered obliquely incident on the half mirror 2. Individual light pulses that have been split are deflected by refractive functions of the wedge prisms constituting the delay elements located on corresponding sides. The light pulses that have been deflected are combined at the common place on the half mirror 2. Thus, in the light pulse multiprocessing unit of Embodiment 4, the operation ranging from the splitting of the light pulse by the half mirror 2 to the combination of the light pulses on the half mirror 2 is repeated three times. The half mirror 2, the three delay elements 331, 332, and 333, and the three delay elements 121, 122, and 123 have predetermined sizes so that the splitting and combination are performed a plurality of times. The light pulse multiprocessing unit thus constructed is arranged and used so that the half mirror 2 is inclined with respect to the incident optical path of the light pulse.

However, the three delay elements 121, 122, and 123 are different from the three delay elements 331, 332, and 333 and are not arranged so that the amount of delay is changed. In other words, the three delay elements 121, 122, and 123 are arranged so that all distances from the half mirror 2 become equal. Whereby, the three delay elements 121, 122, and 123 function like the mirror 12 in the light pulse multiprocessing unit of Embodiment 3.

Other structures, functions, and effects are nearly the same as in the light pulse multi-processing unit of Embodiment 3.

Also, in the light pulse multiprocessing unit of Embodiment 4, two sets of delay elements 331~333 and 121~123 are arranged, three elements for each set, but more delay elements can, of course, be arranged to construct the light pulse multiprocessing unit.

The aspects and embodiments of the light pulse multiprocessing unit of the present invention have been discussed so far. When the light pulse multiprocessing unit described in each of the aspects and embodiments of the present invention and a pulse light source emitting the light pulse toward this light pulse multiprocessing unit are provided, the light pulse generator of the present invention is obtained.

The light pulse multiprocessing unit, light pulse generator, and light pulse multiprocessing method of the present invention are useful in the fields of biology, medicine, and pharmacy in which it is required to measure physical changes caused by a very-short-time domain in a very minute region, using a microscope or measuring instrument, by providing the time delay to irradiate a plurality of illumination light beams by a pump-probe technique or coherent spectrum.

What is claimed is:

1. A light pulse multiprocessing unit comprising:
   splitting means for splitting incident light to produce transmitted light and reflected light;
   a pair of light deflecting means arranged on one side and a remaining side of the splitting means so that the transmitted light and the reflected light, split by the splitting means are deflected and are combined again at a common place on the splitting means; and
   delay means provided on at least one of the one side and the remaining side of the splitting means, for making a substantial optical path difference between optical paths of light split by the splitting means and combined again at the common place on the splitting means to impart a time delay to light traveling along the one side of the splitting means.

2. A light pulse multiprocessing unit according to claim 1, wherein N delay means are arranged on the one side of the splitting means and when the substantial optical path difference due to a first delay means is denoted by D, the substantial optical path difference due to an Nth delay means is $2^{N-1}D$.

3. A light pulse multiprocessing unit according to claim 1 or 2, wherein the delay means are delay elements, each having a refractive index n, and portions of the delay elements through which light is transmitted from the first delay means to the Nth delay means are different in thickness from one another.

4. A light pulse multiprocessing unit according to claim 1 or 2, wherein each of the delay means is provided with a plurality of mirrors and spacings between the plurality of minors are different in a range from the first delay means to the Nth delay means.

5. A light pulse multiprocessing unit according to claim 1 or 2, wherein the pair of light deflecting means are a first minor and a second mirror, arranged parallel to each other.

6. A light pulse multiprocessing unit according to claim 1 or 2, wherein the light deflecting means and the delay means include wedge prisms.

7. A light pulse multiprocessing unit according to claim 1 or 2, wherein the pair of light deflecting means include a pair of wedge prisms.

* * * * *